United States Patent [19]

Johnson

[11] Patent Number: 5,743,852
[45] Date of Patent: Apr. 28, 1998

[54] SPECULUMS

[76] Inventor: William T. M. Johnson, 69 Twin Pine Way, Glen Mills, Pa. 19342-1606

[21] Appl. No.: 632,242

[22] Filed: Apr. 15, 1996

[51] Int. Cl.$^6$ ............................................. A61B 11/02
[52] U.S. Cl. ........................ 600/207; 600/184; 600/208; 600/220; 600/221; 600/223; 606/192; 606/193
[58] Field of Search ............................ 600/184, 199, 600/201, 203, 205, 206, 207, 208, 210, 220, 221, 223, 235, 245; 606/191, 192, 193, 195, 197, 198; 604/96, 98, 104

[56] References Cited

U.S. PATENT DOCUMENTS

| | | | |
|---|---|---|---|
| 2,548,602 | 4/1951 | Greenburg | 600/207 |
| 3,044,461 | 7/1962 | Murdock | |
| 3,132,654 | 5/1964 | Gasper | |
| 3,154,077 | 10/1964 | Lannon | |
| 3,448,739 | 6/1969 | Stark et al. | |
| 3,675,641 | 7/1972 | Fiore | 128/6 |
| 3,709,214 | 1/1973 | Robertson | 128/4 |
| 3,774,596 | 11/1973 | Cook | 600/207 X |
| 3,789,852 | 2/1974 | Kim et al. | 128/347 |
| 3,807,399 | 4/1974 | Morman et al. | 128/263 |
| 3,831,587 | 8/1974 | Boyd | 600/184 X |
| 3,870,036 | 3/1975 | Fiore | 128/6 |
| 3,889,661 | 6/1975 | Fiore | 128/6 |
| 4,501,264 | 2/1985 | Rockey | 128/1 R |
| 4,562,832 | 1/1986 | Wilder et al. | 128/20 |
| 4,641,653 | 2/1987 | Rockey | 128/344 |
| 4,763,653 | 8/1988 | Rockey | 128/344 |
| 4,984,564 | 1/1991 | Yuen | 600/207 |
| 4,994,070 | 2/1991 | Waters | 600/193 X |
| 5,342,385 | 8/1994 | Norelli et al. | 600/193 |
| 5,520,609 | 5/1996 | Moll et al. | 600/207 X |
| 5,545,122 | 8/1996 | Spruill | 600/207 X |

FOREIGN PATENT DOCUMENTS

| | | | |
|---|---|---|---|
| 0206553 | 5/1986 | European Pat. Off. | |
| 0340923 | 4/1989 | European Pat. Off. | |
| 2271283 | 4/1994 | United Kingdom | 600/207 |
| WO 89/00407 | 7/1987 | WIPO | |
| WO 93/07800 | 10/1992 | WIPO | |

*Primary Examiner*—Beverly M. Flanagan

[57] ABSTRACT

Inflatable dual-walled speculums, used for gynecological examinations, that are controllably inflated by the patient with a warmed fluid are provided. A retaining device inserted after inflation of the speculum provides a base and safety for the use of other instruments during the examination. Control of the device by the patient results in a more comfortable examination environment for the patient.

6 Claims, 7 Drawing Sheets

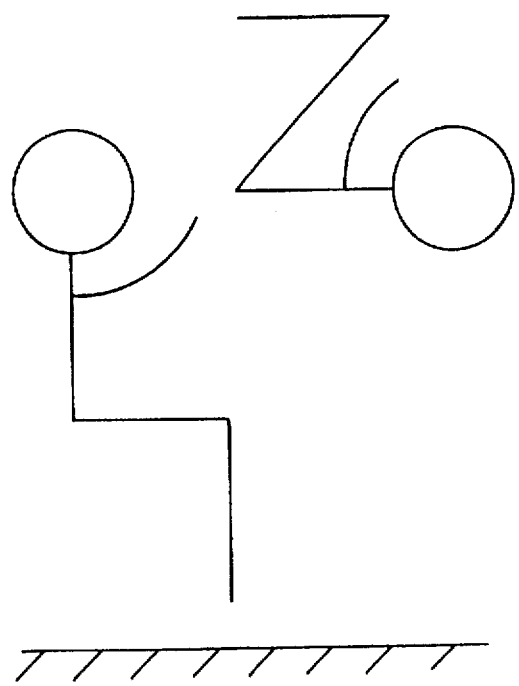
F I G. 9A
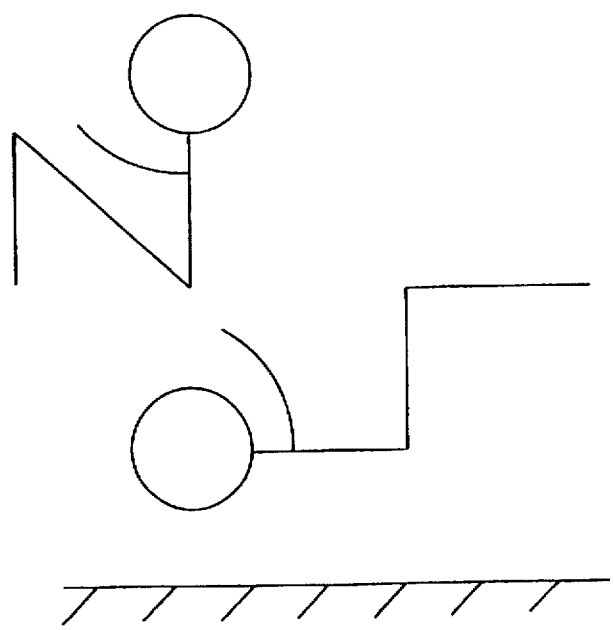
F I G. 9B

SPECULUMS

FIELD OF THE INVENTION

The present invention relates to devices used to assist doctors during gynecological examinations. More particularly, the present invention relates to an inflatable speculum and a system for conducting gynecological examinations in which the inflatable speculum is a primary part of that system. In a preferred embodiment, the speculum is inflated through the use of warm water. Insertion and inflation of the speculum may be controlled by the patient thereby resulting in a more comfortable examination environment for the patient.

BACKGROUND OF THE INVENTION

It has recently been noted that although a safe and inexpensive test has long been available to screen women patients for cervical cancer—and which if widely employed, could all but end the disease—many women still do not have the well-known Papanicolaou smear, or Pap test, routinely administered. (See "They Need Not Die," Apr. 1, 1996, The Philadelphia Inquirer, page C1). Because of this lack of routine and wide implementation, many women will develop cervical cancer and many of those women will unnecessarily die from the disease.

One of the prime reasons women do not have Pap smears routinely taken is due to the discomfort, physical and psychological, that must normally be endured to have the test administered. As reported by the Washington Post, because many women delay or do not have such testing undertaken, treatable gynecological problems progress to untreatable conditions. (Health Section, Dec. 8, 1992, The Washington Post). The Pap smear requires wiping or gently taking a specimen of cells from the neck of a woman's uterus. These cells are applied to a slide and analyzed for cancerous-type abnormalities.

The methods used by gynecologists to conduct pelvic examinations and to administer the Pap smear have required the use of rigid metal speculums to provide the doctor the limited, but necessary, access to the woman's cervix. Prior art speculums are rigid devices, typically constructed of metals such as stainless steel. Use of these devices can be very uncomfortable in part due to the pressure exerted upon the walls of the vagina. Moreover, if the patient is anxious or tense, use of a metal speculum can be even more painful. This tension and the resulting discomfort also results because, by design, the metal speculum is inserted and positioned by the doctor, not the patient. This lack of control can be very uncomfortable and increase psychological and physical tension. As such, many women forego the complete gynecological examination and do not have Pap tests routinely completed. This puts these women at a higher risk of cervical cancer than is acceptable in view of the ease of such preventative testing.

The prior art shows several attempts to provide instruments that expand body cavities such that the doctor is able to observe tissue or complete an examination of the patient. U.S. Pat. No. 2,548,602, Inflatable Dilator, issued to Greenburg, discloses a surgical accessory for examination and treatment of internal body organs which may be inserted into the organ or cavity, that is a soft, flexible, non-rigid instrument, but which may be made rigid to provide access through the instrument. As disclosed, the Greenburg device appears to use web-like ribs within the tube to strengthen the instrument, and does not appear to disclose use for gynecological examinations. Moreover, the Greenburg device has never received acceptance within the medical community.

While U.S. Pat. No. 3,044,461, Procto-Sigmoidoscope, issued to Murdock et al., teaches a procto-sigmoidoscope whose construction permits enlargement and control of the girth of the distal end of the instrument by manipulating means of control located at the proximal end of the instrument, and does disclose use as a vaginal specula, the instrument does not provide any comfort for patients. The Murdock device discloses an instrument that is rigid or metallic and thus provides no basis for increasing any comfort for the patient during the examination.

Finally, International Application No. WO 93/07800, A Speculum, by Muto et al., discloses a speculum having a primary expansion means to expand a body passage in which the speculum is inserted. Although Muto generally teaches a flexible device for use in gynecological examinations that is intended to be more comfortable for patients than traditional specula, the Muto device uses an annulus element in conjunction with longitudinal cells that, as disclosed Muto, necessitates insertion and positioning by the doctor. This requirement does not alleviate tension or fear of the patient which often keeps women from having the testing completed.

The medical community needs a flexible and comfortable speculum that can be easily inserted and positioned by the patient. Moreover, the speculum should be controlled by patient during the examination such that she can attain a level of comfort not available through use of prior art instruments.

The present invention solves these noted problems and deficiencies in addition to other inadequacies exhibited by the prior art. The present invention results have not been achieved in the relevant prior art.

SUMMARY OF THE INVENTION

The above noted problems inadequately resolved by the prior art are resolved by the improved speculums provided in accordance with the present invention.

In a preferred aspect of the invention, an inflatable speculum for use in gynecological examinations, comprises a tube-shaped body section, said body section having an inner wall element and outer wall element sealed together along the edges of the wall elements, thereby forming a fluid-tight envelope, said wall elements being bonded to each other at a plurality of contact areas within said envelope, and means for inflating the body section by introduction of a fluid into the body section envelope.

In other preferred embodiments, the tube-shaped body section may have a narrow and wide end, and the inflating means may be coupled to either the narrow or wide end, thereby resulting in the inflatable speculum having either a narrow interior end or wide interior end.

In another preferred embodiment, the inflation means may be a mechanical pump, a manually-operated pump or a pressurized fluid source.

Another preferred embodiment of the present invention, comprises a release valve coupled to the body section envelope to vent the fluid by aspiration and thereby permit controlled deflation of the speculum.

In another preferred aspect of the present invention, a mechanical device may be incorporated for retaining the inflated speculum in its inflated state. The mechanical device may be a fixed, hollow tube-shaped element that fits within the interior of the inflated speculum body section. In further embodiments of the present invention, a fiber optic light may be affixed to the mechanical retaining device.

Another preferred aspect of the present invention further comprises a removable sleeve that envelopes the body section exterior. In one preferred embodiment, the removable sleeve may be made of plastic strips.

A further preferred aspect of the present invention comprises a removable insertion rod that fits within the speculum body section in the speculum's deflated state; said insertion rod being used to insert and position the deflated speculum prior to inflation; said insertion rod being removed from within the body section after partial inflation of the speculum. In another preferred embodiment, one end of the insertion may be affixed to the removable sleeve thereby allowing for removal of the sleeve through the center of the tube-shaped body section upon withdrawal of the insertion rod.

The claimed invention teaches an improved speculum that provides a more comfortable, both physically and psychologically, examination environment for the patient. Moreover, in a preferred aspect of the invention, a retaining device is inserted into the inflated speculum to provide a fail-safe environment for the patient and doctor. The retaining device in a preferred embodiment may also be used as a base on which other devices may be referenced, including a fiber optic light.

The invention will be best understood by reading the following detailed description of the preferred embodiments in conjunction with the drawings briefly described below.

BRIEF DESCRIPTION OF THE DRAWINGS

For the purpose of illustrating the invention, the attached drawings show several embodiments that are presently preferred. However, it should be understood that the invention is not limited to the precise arrangement and instrumentality shown in accompanying drawings.

FIGS. 9(a and b) are illustrations of the traditional patient and doctor positions during gynecological examinations and the preferred positions capable with the present invention.

DETAILED DESCRIPTION OF THE INVENTION

The present invention is an improved medical device for use by gynecologists conducting pelvic examinations. In a preferred method of operation, the speculum in a deflated state is inserted into the vagina of the patient. Once in position, a fluid is introduced such that a tube-shaped body section that comprises the speculum expands, thereby slowly and gently, expanding the walls of the vagina.

Figure 1:
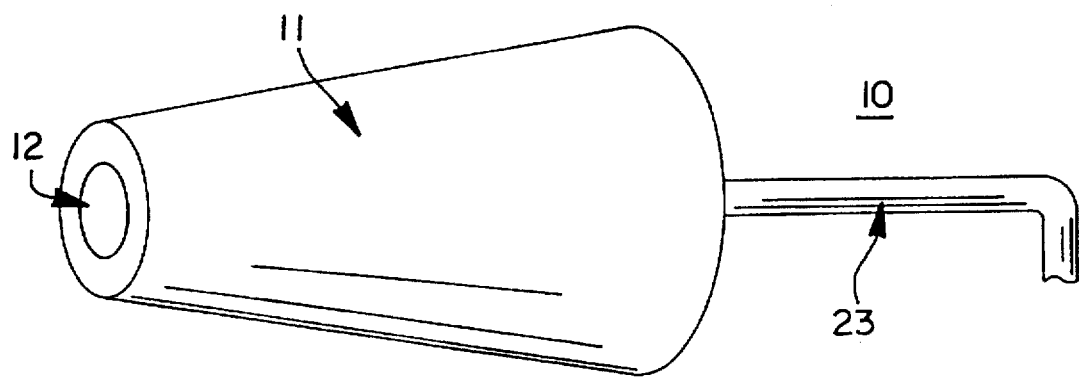
FIG. 1 is a perspective view of a preferred embodiment of the speculum in an inflated state.

Because of the tube-shape of the speculum, as shown in FIG. 1, upon expansion, an open area is provided through the center of the speculum tube-shaped body section, such that sufficient space exists for the doctor to conduct the gynecological examination. In particular, space exists through which the doctor can introduce cotton swabs necessary to obtain cells for Pap tests or to introduce other instruments for further medical tests.

Figure 3:
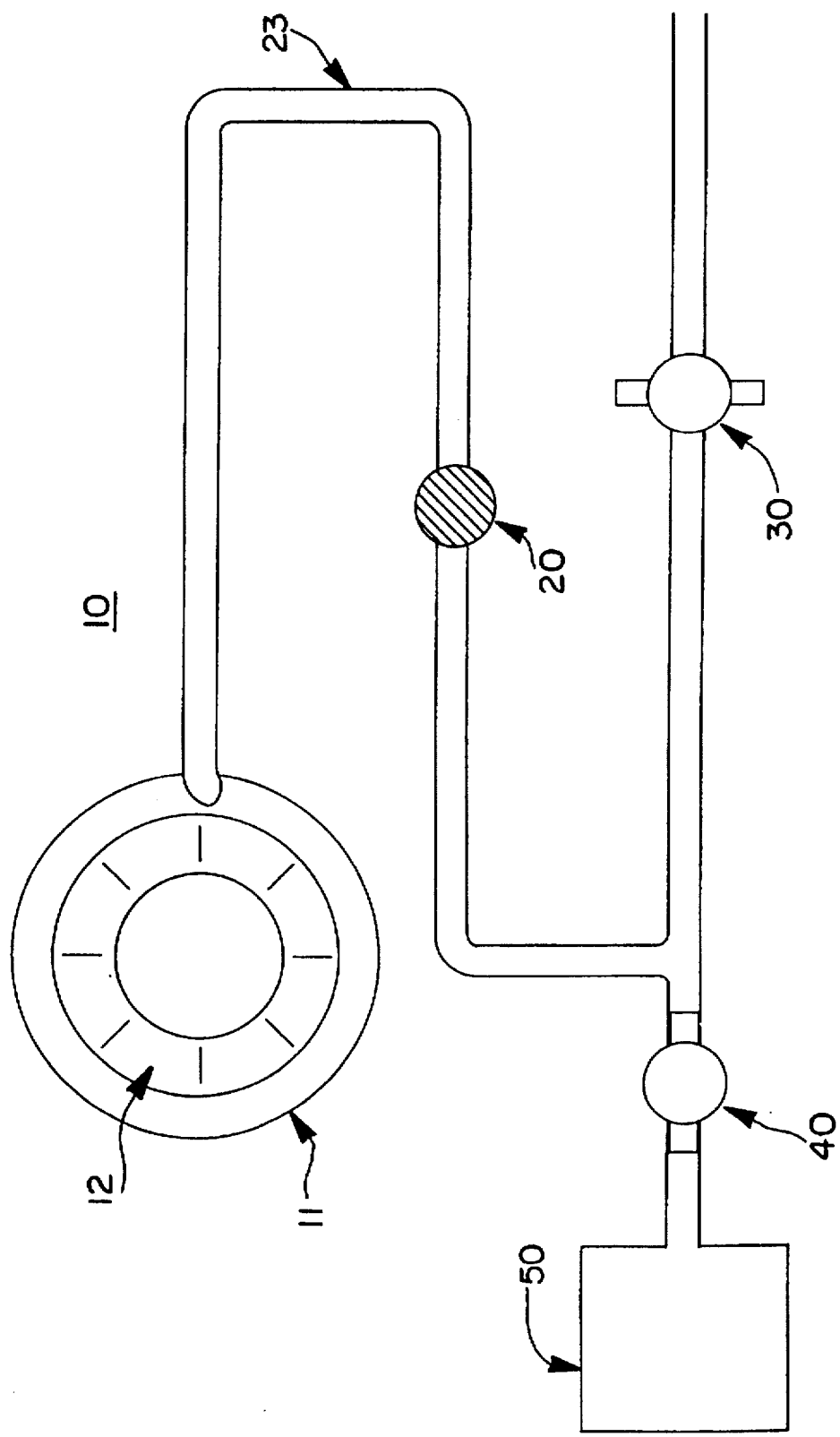
FIG. 3 is a exterior end view of a preferred embodiment of the speculum showing the tubing and valves to controllably introduce and aspirate the fluid to and from the speculum.

In more detail, and as shown in the attached FIGS. 1 and 3, the inflatable speculum 10 has as primary components a dual-walled, tube-shaped body section, and means for introducing a fluid into the tube-shaped body section to "inflate" the speculum 10. The body section comprises an inner-wall element 11 and outer-wall element 12 that are sealed together along their respective edges such that a fluid-tight envelope is formed between the inner and outer wall elements.

Figure 2:
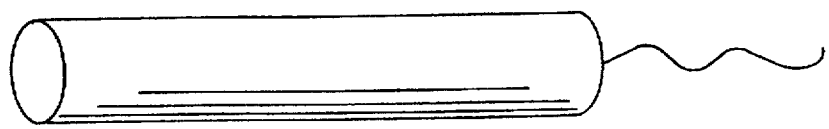
FIG. 2 is a perspective view of a preferred embodiment of the speculum in a deflated state, as compared dimensionally to a tampon.
Figure 2:
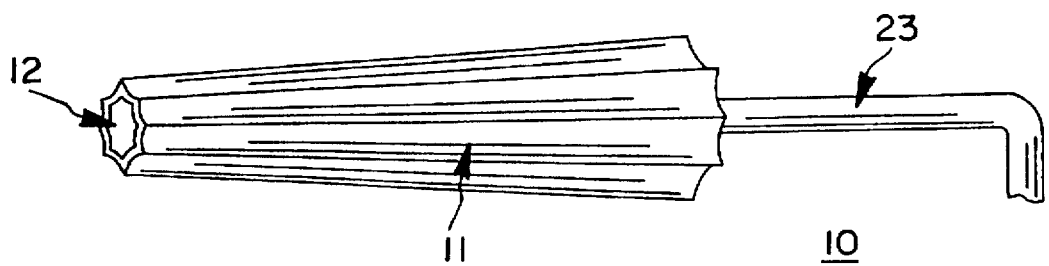

For gynecological examination uses, the inflatable speculum 10 tube-shaped body section dimensions are—in the fully inflated state—approximately within the range of three (3) to six (6) inches in length and one (1) to five (5) inches in diameter. The approximate dimensions for the inflatable speculum 10 in its deflated or packed state are approximately within the range of three (3) to six (6) inches in length and 0.25 to 0.50 inches in diameter. As shown in FIG. 2, the deflated state of the inflatable speculum 10 is comparable, dimensionally, to a typical tampon.

A comparison of the inflated and deflated dimensions shows that during inflation, the tube-shaped body section essentially expands in a radial direction only and does not expand significantly in the longitudinal or length-wise dimension. This is a preferred embodiment with preferred characteristics for use with gynecological speculums. For other uses, including non-gynecological uses, the present invention inflatable speculum could be designed to expand equally in both longitudinal and radial directions, or expand substantially in the longitudinal direction.

Figure 4A:
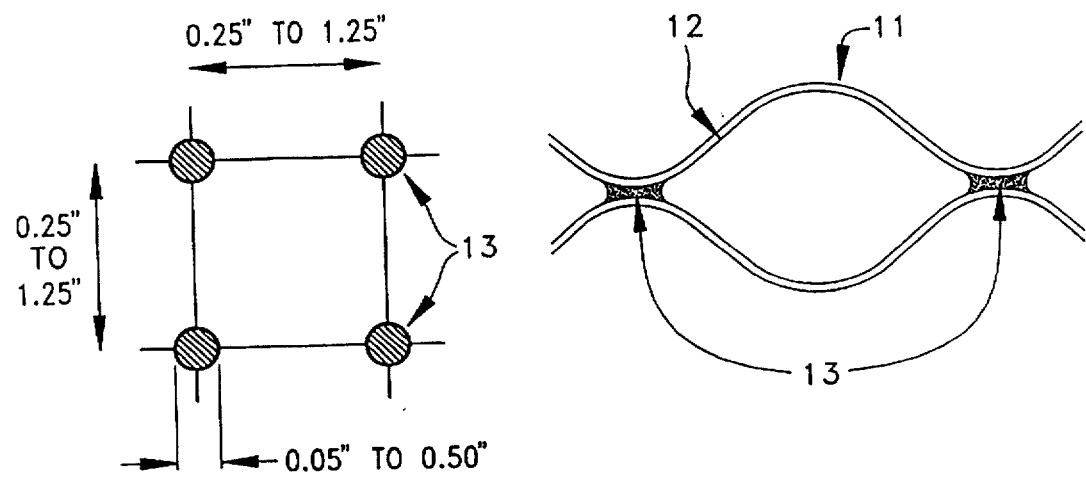
FIGS. 4(a and b) are top and cross-sectional views of preferred embodiments of the grid pattern and spacing for the bonded areas between the inner and outer walls of the inflatable speculum.
Figure 4B:
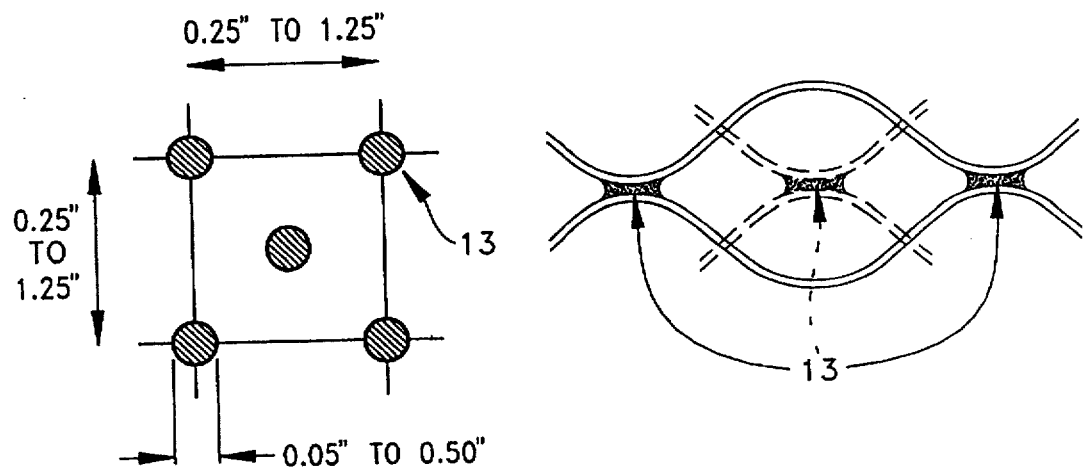

In a preferred embodiment, the inner and outer wall elements are bonded to each other at a plurality of contact areas 13 within the fluid-tight envelope. These contact areas 13 are incorporated within the envelope as shown in FIGS. 4(a) and 4(b), in part, to maintain the inner diameter of the tube-shaped body section during inflation. Without these contact areas 13, the inner wall 12 would simply balloon inward during inflation, thereby closing off the tube section inner diameter. Maintenance of a clear inner opening of the tube-shaped body section is necessary for the doctor to conduct the examination.

The pattern of the contact areas 13 between the inner 11 and outer wall elements 12 can be varied extensively. In a preferred embodiment, an orthogonal grid pattern as shown in FIG. 4(a), has been shown to be quite effective. The diameter of the bond areas 13 preferably should be approximately within the range of 0.05 to 0.50 inches in diameter. While the bond areas 13 are shown in FIGS. 4(a) and 4(b) to be essentially circular, the shape of the bond area 13 can be orthogonal and still be equally effective.

In the grid pattern of bond or contact areas 13, the spacing between the bond areas 13 preferably should be approximately within the range of 0.25 to 1.25 inches apart from each other as shown in FIGS. 4(A) and 4(B). These approximate ranges have been determined from an analysis, experimentation and understanding of the size of a standard gynecological speculum as described above. The present invention inflatable speculum used for other than gynecological purposes could result in bond area sizing and grid pattern spacing smaller or larger than the preferred dimensions noted above.

While in a preferred embodiment, it has been determined that a grid pattern of contact areas 13 works well, other patterns of contact between the inner 11 and outer walls 12 may be equally effective, including contact lines along the length of the body section or contact lines along the circumference of the body section.

Figure 5:
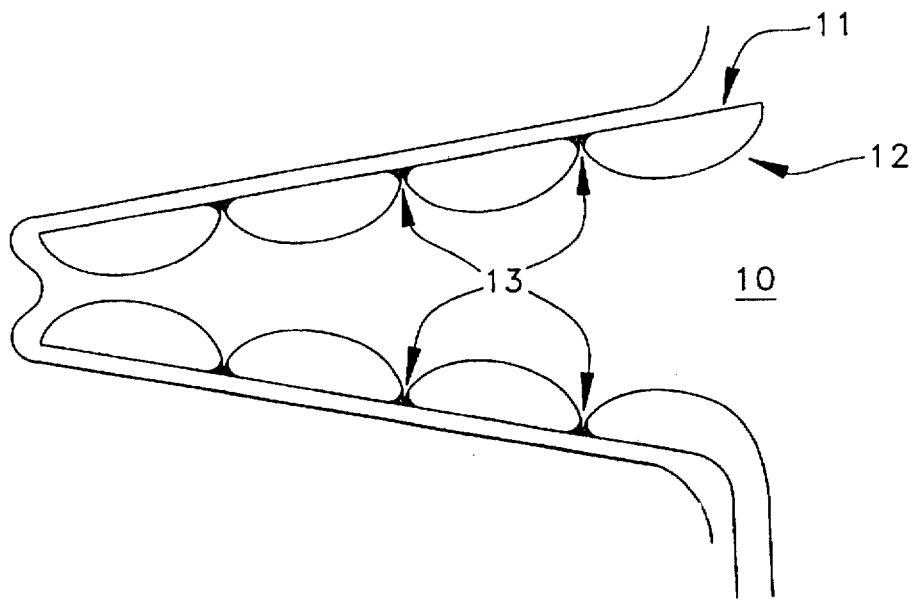
FIG. 5 is a side view of a preferred embodiment of the speculum with a narrow interior end, in an inflated state.

Although the body section of the inflatable speculum 10 is described as tube-shaped, it has found that embodiments using a "cone-shaped" body section have equal effectivity. As shown in FIGS. 1 and 5, an inflatable speculum 10 with a narrow interior end may be used. Similarly, where a doctor requires a wider area of the cervix to conduct the examination, in another preferred embodiment, an inflatable speculum 10 with a wider interior end may be used, as shown in FIG. 6.

In a preferred embodiment, warm water can be used as the fluid introduced into the speculum to inflate the device. The use of a warm liquid addresses the problem of having a rigid (and often cold) metal device placed against sensitive body tissues. Standard gynecological metal speculums, constructed of stainless steel are rigid, unyielding metal objects that cause a patient to tense prior to use. This tension results, in part, from the potential discomfort and pain due to the unyielding nature of the speculum and due to the fact that the doctor inserts the speculum. The lack of control on the part of the patient results in psychological tension. By its nature, water contained within a pliable envelope is not unyielding. Therefore, the present invention solves the problem of patient discomfort that results from the use of rigid metal speculum. In a preferred embodiment, the warm water could have a temperature of approximately normal body temperature, thereby solving the discomfort through use of a cold metal speculum.

Although as explained herein, the preferred inflating fluid is warm water, other liquids can be used with equal effectivity, including without limitation, a saline solution. Moreover, while other limitations or problems may be presented, in another embodiment, warmed air could be used as the introducing/inflating fluid.

Figure 6:
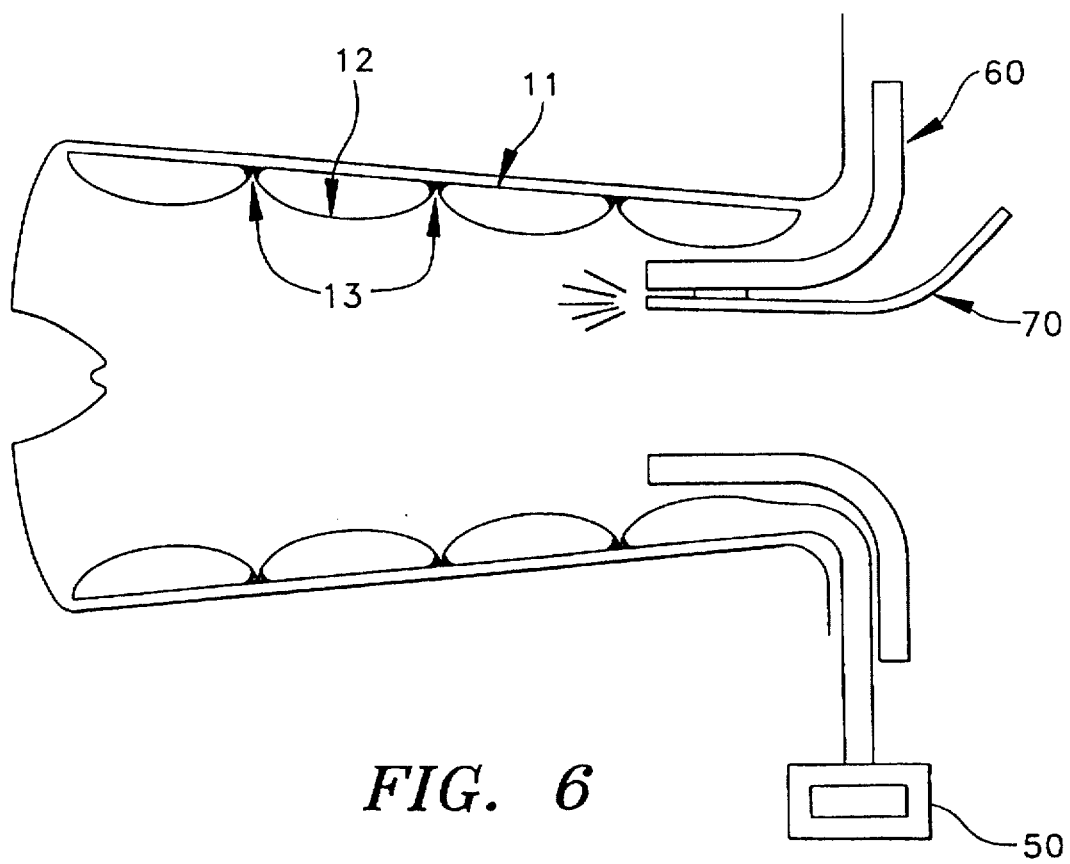
FIG. 6 is a side view of a preferred embodiment of the speculum with a wide interior end, in an inflated state, and with a retaining cone inserted within the inflated speculum with an attached fiber optic light.

The fluid used to expand the speculum from its deflated state to the inflated state may be introduced to the body section envelope through, in a preferred embodiment, a tube 23 as shown in FIGS. 1 and 6. Because most body cavities to be examined are not open in the natural state, the introduction of the expanding fluid must be through a fluid source having some pressure. In a preferred embodiment, a mechanical pump may be used to introduce the fluid into the speculum envelope. Equally productive however, in another preferred embodiment, a pressurized fluid source could be used to inflate the speculum. One standard pressurized fluid source is simply a faucet 40.

The introduction of the fluid into the body section to expand the speculum should be variably controlled such that the rate of expansion of the speculum is neither too sudden nor too slow. The control of the rate of fluid introduction into the speculum may be accomplished by a release or needle valve 20 as shown in FIG. 3. In this embodiment, the patient can easily control the rate of expansion and in addition to the extent of expansion. As such, the patient will be more comfortable knowing that she has direct control of the device within her body. In a further preferred embodiment, instead of the above noted mechanical pump or pressurized fluid source, a manually operated pump could be used as the fluid source to introduce the fluid into the speculum envelope. Again, the present invention provides the patient with an overall more comfortable examination environment, in large part because she has control over the devices within her body.

As also shown in FIG. 3, a preferred embodiment of the present invention comprises a release valve 30 to deflate the speculum by release of the inflating fluid through aspiration. The release valve 30 can be coupled with the body section envelope or along the tubing 23. Similar to the introduction of the fluid to expand the speculum, the release of the fluid and speculum pressure, in a preferred embodiment, could be variably controlled such that deflation is not too rapid or too slow. Moreover, because the release valve 30 may be coupled to the body section envelope, the patient again may control the rate of deflating the speculum.

Another preferred embodiment for deflating the speculum could be a mechanical pump as described above, that has the capability of being reversible and thereby could evacuate the speculum envelope. Similarly, a second pressurized fluid source could be used to aspirate the fluid within the speculum 10 as a result of the physical effect of fluid entrainment.

In addition to the above described elements of the inflatable speculum 10, additional components have been invented to be used in conjunction with the inflatable speculum body section. In one preferred aspect of the improved speculum system, a mechanical device may be used with the inflatable speculum to retain the inflated body section in its inflated state. FIG. 6 shows one example of a retaining mechanical device, being a fixed tube-shaped or cone-shaped component 60.

The retaining device 60 fits within the inflated speculum 10. There are several purposes for the retaining device 60. First, the device provides a "fail-safe" environment within which the doctor can conduct her examination. For example, if the inflated speculum 10 were to deflate accidentally, the retaining device 60 would maintain the opening for the doctor and prevent injury to the patient due to instruments used by the doctor during the examination at the time of the accidental deflation.

Moreover, the fixed retaining device provides a means for introducing other instruments, including a fiber-optic light source 70. Because of the pliable and soft characteristics of the body section of the inflatable speculum 10, it can not be used as a fixed support against which other instruments could be applied or attached.

Figure 7:
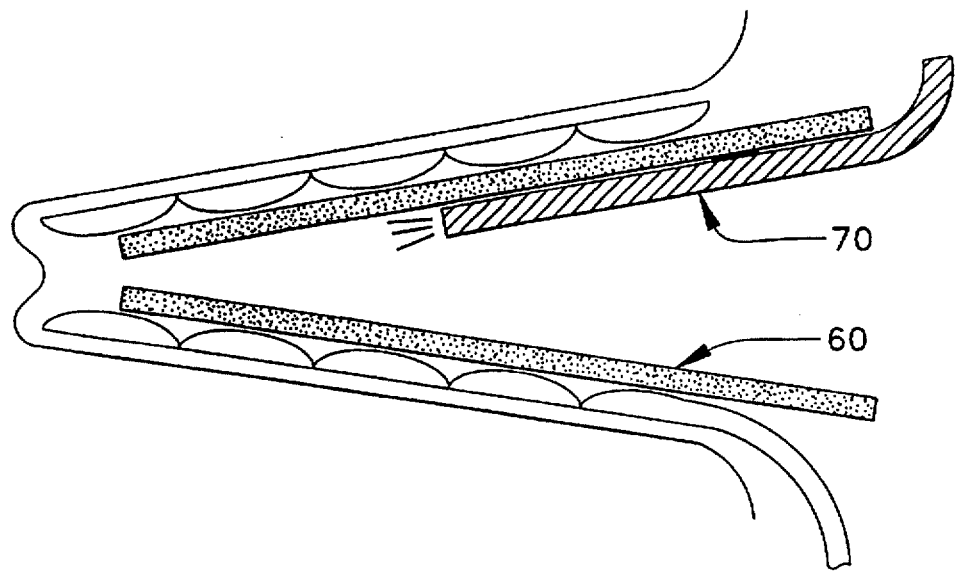
FIG. 7 is a side view of a preferred embodiment of the speculum with a narrow interior end, in an inflated state, and with a retaining cone inserted within the inflated speculum and with an attached fiber optic light.

An example cone shaped component 60 being used in conjunction with the light source 70, to facilitate the examination is shown in FIG. 7.

Figure 8:
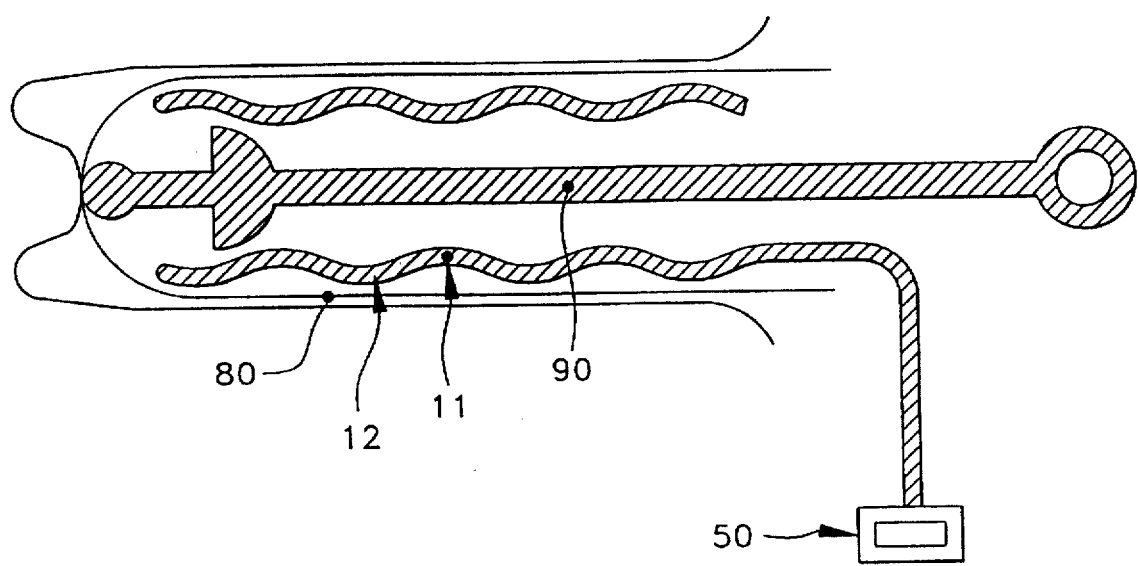
FIG. 8 is a side view of the improved speculum system including the insertion rod and plastic sleeve prior to removal of the rod and sleeve.
Figure 10:
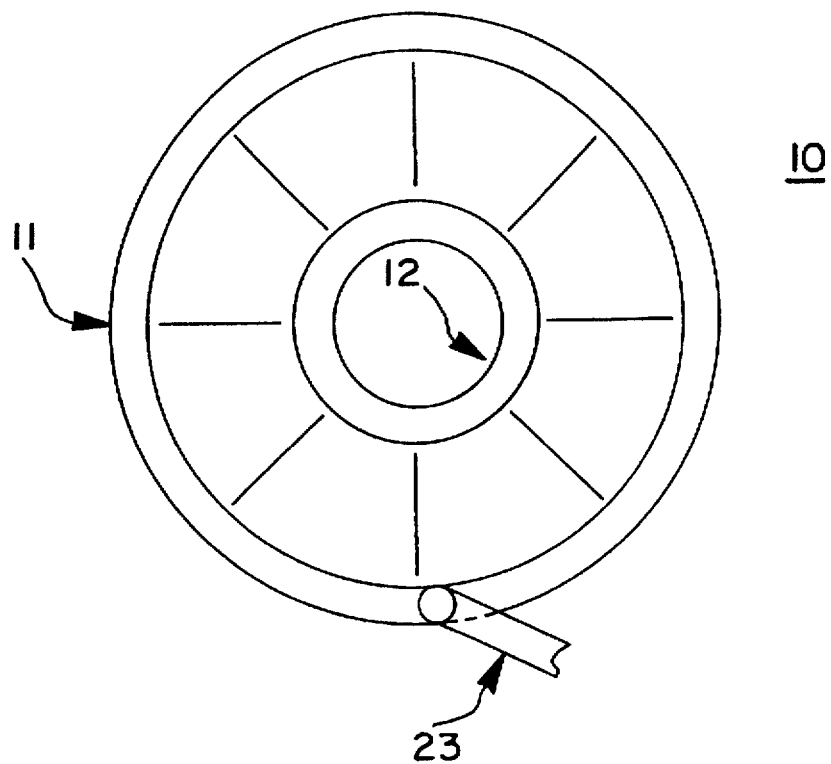
FIG. 10 illustrates the interior view of the invention viewed along the interior longitudinal axis.

In another preferred aspect of the improved speculum system, as shown in FIG. 8 a removable sleeve 80 may be used to act as a seal and protective cover around the exterior of the speculum 10 during packing and shipment prior to use of the speculum 10 as a medical instrument. One preferred embodiment of the removable sleeve aspect, comprises the removable sleeve 80 as a plurality of plastic strips that run the length of the inflatable speculum 10. The embodiment of a plastic sleeve 80 provides the additional attribute that plastic generally has a reduced level of static friction, and thus insertion of the deflated speculum will be easier and reduce the level of discomfort of the patient.

The embodiment of the present invention with the plastic sleeve is used such that after insertion of the inflatable speculum 10, the speculum is only partially inflated. Thereafter, the plastic strips 80 would be removed through the center of the body section.

In another preferred aspect of the present invention, to facilitate the insertion and positioning of the inflatable speculum 10 by the patient, in addition to aiding in the removal of the removable sleeve 80, an insertion rod 90 as shown in FIG. 8 may be incorporated. The insertion rod 90 is positioned inside the tube-shaped body section such that one end of the insertion rod is affixed to the removable sleeve as shown in FIG. 8 at point 91. The other end of the insertion rod 90 extends slightly outside of the speculum body section. Accordingly, as described above, use of this aspect of the present invention allows the patient to insert and position the deflated speculum within her vagina using the insertion rod 90. After partial inflation of the speculum 10—again, controlled by the patient—the patient then removes the insertion rod 90 which necessarily withdraws the removable sleeve 80 through the center of the speculum tube-shaped body section due to the attachment at point 91. Thereafter, at the direction of the doctor, the patient can then further inflate the speculum at a rate and to an extent that is comfortable.

In a preferred aspect of the present invention, the inflatable body section is removable and disposable, such that after each use the body section is disposed. Moreover, with use of the removable sleeve 80, the inflatable speculum may be shipped in sterilized packaging.

In conjunction with the use of the present invention improved speculum, a preferred manner of conducting a gynecological examination may be used. Instead of the traditional position in which the patient is prone with the doctor sitting in front of the patient as shown in FIG. 9(a), with the present invention, the patient can be sitting, more or less in a normal sitting position, and the doctor can be inclined under the patient as shown in FIG. 9(b). This manner of examination is likely to be more psychologically comfortable for many patients. The present invention permits this manner of examination because it is the patient who inserts and positions the speculum, not the doctor as is required with rigid metallic speculums.

The foregoing detailed description teaches certain preferred embodiments of the present invention for improved speculums. While preferred embodiments have been described and disclosed, it will be recognized by those skilled in the art that modifications are possible and that such modifications are within the true scope and spirit of the present invention. It is likewise understood that the attached claims are intended to cover all such modifications.

List of Figure Reference Numerals 10 double-walled inflatable speculum
11 inflatable speculum outer wall element
12 inflatable speculum inner wall element
13 contact areas of inner and outer wall elements
23 flexible tubing for introducing the inflating fluid
20 fluid release valve for introducing the fluid
30 fluid release valve for evacuating the fluid
40 fluid release valve for introducing the fluid from a fluid source or pump
50 fluid source
60 fixed retaining cone
70 fiber optic light
80 removable speculum sleeve
90 insertion rod
91 insertion rod / removable speculum sleeve contact area

What is claimed is:

1. An inflatable speculum for use in gynecological examination, comprising:

a tube-shaped body section, said body section having an inner wall element and outer wall element sealed together along the edges of the wall elements, thereby forming a fluid-type envelope, said wall elements being bonded to each other at a plurality of contact areas within said envelope;

means for inflating the body section by introducing a fluid into the body section envelope;

wherein the plurality of contact areas comprise a grid pattern;

wherein further said grid pattern comprises circular bonded areas that are approximately within the range of 0.05 to 0.50 inches in diameter.

2. An inflatable speculum for use in gynecological examination, comprising:

a tube-shaped body section, said body section having an inner wall element and outer wall element sealed together along the edges of the wall elements, thereby forming a fluid-type envelope, said wall elements being bonded to each other at a plurality of contact areas within said envelope;

means for inflating the body section by introducing a fluid into the body section envelope;

wherein the inflation means is a pressurized fluid source; and wherein the inflated speculum is deflated through the use of an aspirator to remove the fluid introduced in the body section envelope.

3. An improved medical speculum system, comprising:

an inflatable speculum, comprising a tube-shaped body section, said body section having an inner wall element and an outer wall element sealed together along the edges of the wall elements, thereby forming a fluid-tight envelope, said wall elements being bonded to each other at a plurality of contact areas within said envelope;

means for inflating the body section envelope;

a mechanical device for retaining the inflated speculum in its inflated state; and a removable plastic sleeve that envelopes the speculum body section exterior wherein the removable sleeve is a plurality of plastic strips.

4. The improved medical speculum system of claim 3, further comprising a removeable insertions rod that fits within the speculum body section in the speculum's deflated sate; said insertion rod being used to insert and position the deflated speculum prior to inflation; said insertion rod being removed from within the body section after partial inflation of the speculum.

5. The improved medical speculum system of claim 3, further comprising a removable insertion rod that fits within the speculum body section in the speculum's deflated state such that one end of said insertion rod extends through the body section and is affixed to the removable sleeve, and the other end of the insertion rod extends outside of the body section; said insertion rod being used to insert and position the deflated speculum prior to inflation; said insertion rod being removed from within the body section after partial inflation of the speculum thereby also withdrawing the removable sleeve through the speculum body section.

6. An improved medical speculum system, comprising:
- an inflatable speculum, comprising a tube-shaped body section, said body section having an inner wall element and an outer wall element sealed together along the edges of the wall elements, thereby forming a fluid-tight envelope, said wall element being bonded together at a plurality of contact areas within said envelope wherein said contact areas form a grid pattern;
- means for inflating the body section by introducing a fluid into the body section envelope;
- a rigid medical device for retaining the inflated speculum in its inflated state, said rigid medical device being inserted and positioned within the inflated speculum after inflation;
- a removable plastic sleeve that covers the speculum body section exterior; and
- a removable insertion rod that fits within the speculum body section interior in the speculum's deflated state such that one end of said insertion rod extends through the body section and is affixed to removable sleeve, and the other end of the insertion rod extends outside of the body section, said insertion rod being used to insert and position the deflated speculum prior to inflation;
- wherein said insertion rod is removed from within the body section interior after partial inflation of the speculum thereby also withdrawing the removable sleeve through the speculum body section.

* * * * *